(12) United States Patent
Van De Kerkhof et al.

(10) Patent No.: US 8,746,966 B2
(45) Date of Patent: Jun. 10, 2014

(54) THERMOANALYTICAL INSTRUMENT

(75) Inventors: Ernst Van De Kerkhof, BD Sittard (NL); Paul Pieter Willem Van Grinsven, Maasmechelen (BE)

(73) Assignee: Mettler-Toledo AG, Greifensee (CH)

( * ) Notice: Subject to any disclaimer, the term of this patent is extended or adjusted under 35 U.S.C. 154(b) by 767 days.

(21) Appl. No.: 12/466,068

(22) Filed: May 14, 2009

(65) Prior Publication Data

US 2009/0310644 A1    Dec. 17, 2009

(30) Foreign Application Priority Data

Jun. 13, 2008  (EP) .................................... 08158196

(51) Int. Cl.
*G01K 17/00* (2006.01)
*G01N 25/20* (2006.01)

(52) U.S. Cl.
USPC .............. 374/31; 374/11; 374/165; 374/179; 422/51; 436/147

(58) Field of Classification Search
USPC ........... 374/31–39, 10, 11, 12, 179, 112, 113, 374/29, 30, 43, 100–102, 137, 165; 219/497; 422/51; 436/147
See application file for complete search history.

(56) References Cited

U.S. PATENT DOCUMENTS

| | | | | |
|---|---|---|---|---|
| 3,263,484 A * | 8/1966 | Watson et al. | .................. | 374/11 |
| 3,995,485 A * | 12/1976 | Beyer et al. | .................. | 374/33 |
| 4,255,961 A * | 3/1981 | Biltonen et al. | ................ | 374/11 |
| 4,848,921 A * | 7/1989 | Kunze | ............................ | 374/11 |
| 5,672,289 A | 9/1997 | O'Neill | | |
| 5,967,659 A * | 10/1999 | Plotnikov et al. | ................ | 374/11 |
| 5,973,299 A * | 10/1999 | Reader, Jr. | .................... | 219/486 |
| 6,079,873 A * | 6/2000 | Cavicchi et al. | ................ | 374/10 |
| 6,370,939 B2 * | 4/2002 | Smith et al. | ................. | 73/19.03 |
| 6,530,686 B1 * | 3/2003 | Nakamura | ...................... | 374/11 |
| 6,572,263 B1 * | 6/2003 | Refalo et al. | ................... | 374/31 |
| 6,583,391 B2 * | 6/2003 | Jorimann et al. | ............. | 219/497 |

(Continued)

FOREIGN PATENT DOCUMENTS

CN    1598558 A    3/2005
EP    0267308 A2   5/1988

(Continued)

OTHER PUBLICATIONS

Lagnier, R., "The measurement of low temperature specific heats using dynamic differential calorimetry", Cryogenics, Jun. 1977, pp. 349-353, vol. 17, No. 6, Elsevier, Kidlington, Great Britain.

(Continued)

*Primary Examiner* — Gail Verbitsky
(74) *Attorney, Agent, or Firm* — Standley Law Group LLP

(57) ABSTRACT

A thermoanalytical instrument, and especially a differential scanning calorimeter, has first and second measurement positions, a heater and a temperature sensor associated with each of the measurement positions, and a controller. The controller, which has an associated means for setting a predetermined temperature program, controls a heating power of the first heater to cause the temperature measured at the first position to follow the temperature program. The controller also controls both heaters to eliminate any temperature difference between the measured first and second temperatures. The controller also provides a means for determining the lower of the measured first and second measured temperatures and applies additional power to the heater associated with that lower measured temperature.

9 Claims, 8 Drawing Sheets

(56) References Cited

U.S. PATENT DOCUMENTS

| | | |
|---|---|---|
| 6,632,015 B2 | 10/2003 | Nagasawa |
| 7,448,796 B2 * | 11/2008 | Schick .......................... 374/31 |
| 7,470,058 B2 | 12/2008 | Hutter et al. |
| 2006/0256836 A1 | 11/2006 | Hütter et al. |
| 2008/0071494 A1 * | 3/2008 | Reading ........................ 702/130 |
| 2009/0310646 A1 * | 12/2009 | Schenker ....................... 374/31 |
| 2010/0195695 A1 * | 8/2010 | Van De Kerkhof et al. .... 374/31 |
| 2013/0288386 A1 * | 10/2013 | Fon et al. ...................... 436/501 |

FOREIGN PATENT DOCUMENTS

| | | |
|---|---|---|
| EP | 1215484 A2 | 6/2002 |
| JP | 2006-105935 A | 4/2006 |
| SU | 1067375 A * | 1/1984 |

OTHER PUBLICATIONS

Van Herwaarden, A.W., "Overview of calorimeter chips for various applications", Thermochimica Acta, 2005, pp. 192-201, vol. 432, Elsevier.

* cited by examiner

THERMOANALYTICAL INSTRUMENT

CROSS-REFERENCE TO RELATED APPLICATIONS

This application claims a right of priority under 35 USC §119 from European patent application 08 15 8196.9, filed 13 Jun. 2008, the content of which is incorporated by reference as if fully recited herein.

TECHNICAL FIELD

The present invention relates to a thermoanalytical instrument, in particular a differential scanning calorimeter, and to a method for operating such an instrument.

BACKGROUND OF THE ART

Thermoanalytical instruments, such as differential scanning calorimeters (DSC), are used to measure different characteristics and properties of a sample which is exposed to a temperature program.

A DSC is utilized to record temperature-related changes of the physical or chemical characteristics of a sample. These are for example heat measurements related to exothermic or endothermic events accompanying transitions and other effects occurring in a sample which is subjected to temperature changes. The changes of the sample are determined in relation to a reference, which can be an empty reference position or a suitable reference material. Depending on the type of DSC the reference or sample material can be placed directly on a respective measurement position or it can be placed in a suitable crucible, which is then placed on the measurement position.

Two main control principles for a DSC are well known, these are the heat flux principle and the power compensation principle. In the following, an example for a power compensated DSC will be discussed in more detail.

Power compensation is usually implemented into a thermoanalytical instrument by placing and separately controlling an additional heater, often referred to as compensation heater, at the sample position. The sample position, the reference position as well as any material placed on one of said positions are subjected to a temperature program, which is applied by the main heaters of the reference position and the sample position. The main heater of the sample position merely mimics the heating power delivered by the heater of the reference position. Said compensation heater is used to deliver any excess power needed for heating the sample in order to take it through endothermic phase transitions, while the temperature difference between the sample and the reference positions is controlled to remain substantially zero. Excess or compensation power is also needed for performing cooling runs, in which case the compensation heater applies a certain heat amount to the sample at the beginning of the experiment, which is gradually reduced during the experiment.

The reference position of a power compensated DSC is also equipped or in thermal contact with another compensation heater, which is set to a fixed offset voltage and provides a constant compensation power. In relation to said fixed reference offset the actual heating power demand of the sample expressed as the sample voltage can either be positive or negative. Such a power compensated DSC is for example disclosed in U.S. Pat. No. 6,632,015 B2 to Nagasawa.

For the analysis of very thin films and particles with masses in the microgram or even nanogram range different chip-based calorimeters were developed, which are often based on silicon technology. An overview over different uses of these chip calorimeters, such as e.g. high-speed DSC, is given by A. W. van Herwaarden "Overview of Calorimeter Chips for Various Applications", Thermochimica Acta, 432 (2005), 192-201.

The realization of the power compensation principle for a chip-type DSC enhances several drawbacks of this principle, which were so far disregarded as being negligible. Depending on the setup, these drawbacks relate for example to the limited negative compensation headroom, the offset temperature as well as a baseline offset, drift and curvature.

Limited negative compensation headroom can lead to a cutoff of the measurable heat flow and can result in false or incomplete results. For power compensation the amount of 'negative' compensation power is limited by the offset compensation power set at the reference position. Therefore, the reference offset power has to be adapted in relation to the investigated sample. For an unknown sample it might even take several experimental runs to determine the appropriate reference offset power, which can result in wasting precious sample material as well as being time consuming.

Said reference offset power generates an offset temperature, which reduces the operational temperature range of the instrument. By reducing the reference offset power the offset temperature can also be reduced in order to expand the operational temperature range, but unfortunately this will increase the problem related to the limited negative compensation headroom. In order to ensure sufficient headroom e.g. for very fast cooling experiments, the resulting offset temperature can amount to several tens of degrees Celsius.

The baselines of the resulting DSC curves can also be offset due to the amount of offset power supplied at the reference position. Additionally, even when the offset voltage at the reference position is kept constant, the resulting offset power will vary with temperature as the resistance of the reference compensation heater depends on the temperature. This effect can result in an unwanted baseline drift and/or baseline curvature, which can further be superimposed by intrinsic physical differences between the sample and reference positions.

Therefore, the object of this invention is to provide a thermoanalytical instrument, in particular a differential scanning calorimeter (DSC), as well as a compensation principle for said thermoanalytical instrument, which overcomes the drawbacks of the power compensation principle.

SUMMARY

In a first aspect, the invention relates to a thermoanalytical instrument, in particular a DSC, comprising a first and a second measurement position, means for setting a predetermined temperature program of temperature target values versus time, a first heater associated with the first measurement position, a second heater associated with the second measurement position, a first sensor for measuring a temperature of the first measurement position, a second sensor for measuring a temperature of the second measurement position, and a controller. Said controller controls the heating power of said first heater so as to cause said measured first temperature to essentially follow said temperature program and additionally said controller controls said first and second heaters so as to essentially cause any difference between said first and second measured temperatures to become zero. The thermoanalytical instrument is characterized in that the controller comprises means to determine which of said first and second temperatures is lower and applies an additional power to the heater which is associated with the measurement position having said lower measured temperature.

In other words, the controller dynamically controls either the first heater or the second heater in order to compensate for any temperature difference, also referred to as differential temperature, arising between the first and the second measurement position by applying additional heating power to the cooler one of the measurement positions.

The invention will be mainly described in relation to a DSC as an exemplary thermoanalytical instrument according to the invention. Preferably one of the measurement positions is referred to as sample position and the other as reference position, wherein any sample or reference material can either be placed directly on the respective measurement position or in a suitable crucible which is then placed on the respective measurement position.

The thermoanalytical instrument according to the invention, in particular a DSC, overcomes the drawbacks of a power compensated instrument, especially its quite rigid reference compensation offset by introducing a dynamic compensation approach. Instead of supplying compensation power or additional power only to the sample position, as it is know for the power compensation principle, in the thermoanalytical instrument according to the invention the compensation power is applied alternatively to one or the other of the measurement positions depending on where and when it is required. The compensation power can either be supplied directly through the first or the second heater or through individual compensation heaters associated with the respective measurement positions.

In an exemplary embodiment, the thermoanalytical instrument further comprises a first compensation heater associated with the first measurement position and a second compensation heater associated with the second measurement position. The temperature program can be applied to each measurement position through the respective heater. With the determination means comprised in the controller the measurement position having the lower temperature is determined and the controller applies an additional power to the compensation heater associated with the measurement position having said lower measured temperature.

The controller dynamically controls either the first compensation heater or the second compensation heater in order to compensate for a temperature difference or differential temperature arising between the first and the second measurement position. The separation of the heater functions by applying the temperature program through the first and second heaters and the additional power through one of the compensation heaters is advantageous to improve the signal-to-noise ratio. The additional or compensation power can be alternatively supplied to either of the measurement positions, depending on which position is cooler and therefore has the highest momentary power demand. The compensation power will always be supplied as a non-negative power value, in particular as a non-negative compensation voltage, which is transformed into a compensation power and further into a compensation temperature.

As a way to distinguish between these two methods of operating a DSC, the known approach will be referred to as power compensation and the approach according to the invention as dynamic compensation.

Preferably, the controller comprises a first control loop for controlling the application of the temperature program and a second control loop for controlling the compensation of the differential temperature. The differential temperature is compensated by applying additional power to the cooler one of the measurement positions.

Advantageously, said determination means are comprised in the second control loop so that the sign of the differential temperature between the first and the second measurement position can be determined. The differential temperature is determined from the difference between the measured first and second temperatures either at predetermined time intervals or continuously.

Depending on the setup, the controller can either be analog or digital. An analog controller preferably comprises a PID controller for each control loop. A digital controller allows a more flexible approach and can for instance be designed as a fuzzy control system.

In an exemplary embodiment, each sensor comprises a thermopile arrangement with at least one thermocouple for measuring the first or second temperature. Especially for DSC instruments several designs of thermopile arrangements are known, ranging from a single thermocouple to complex designs comprising patterns of thermocouples arranged in one or more layers beneath and/or around each measurement position.

For the dynamic compensation it is advantageous, when the first and second measurement position exhibit an intrinsic symmetry, so that any differential temperature can be attributed to an excess heat flow into or out of the sample and only few to no error corrections due to differences in the composition, mass or other properties of the measurement positions have to be made for the determination of the sample's properties. The sought properties are usually determined from said additional power needed to compensate any differential temperature.

The measurement positions can be arranged on a common holder or each measurement position can be arranged on a separate holder, wherein it is essential that the measurement positions are thermally decoupled.

Depending on the quantity of measurements to be run on a single sample material or the quantity of experiments to be performed under similar conditions, it can be advantageous to provide an instrument with multiple pairs of first and second measurement positions, wherein the measurement positions can be arranged on a common holder or on individual holders comprising one or more measurement positions.

Controlling a thermoanalytical instrument with the dynamic compensation gives rise to further challenges which will be described in more detail below.

A thermoanalytical instrument, such as a DSC, comprising first and second heaters and first and second compensation heaters can exhibit several switches of the compensation power between the compensation heaters during a single experimental run. As long as the switching takes place upon reversal of the scanning direction, e.g. from cooling to heating or vice versa, this is of no concern and can be neglected. Data obtained during these direction changes—as known from power compensation—are usually not included in the generation of any experimental results. However, said switching can also occur during a scan or even while a physical or chemical transition takes place in the sample. In that event, artifacts caused by the switching can result in inaccurate data and finally in inaccurate experimental results. Switching between the compensation heaters can occur more frequently for slow measurements, when the signal is so small that the absence of absolute symmetry between the sample and reference positions can cause zero-crossings during a scan, or during cold crystallization experiments. For these experiments fast switching with respect to the data acquisition frequency can be crucial.

According to a second aspect, the invention relates to a thermoanalytical instrument, in particular a DSC, which further comprises means for restricting the supply of said additional power so that said additional power is only supplied to one of the heaters or compensation heaters at the same time.

Preferably the restriction means activate only one of the heaters or one of the compensation heaters according to a proportion of the temperature difference between the first and the second measurement position.

For an instrument with first and second compensation heaters this means that due to said restriction means the compensation power in form of the compensation voltage is still offered to all compensation heaters but an electric current will only be supplied to the appropriate compensation heater, which is chosen in accordance with the heating power demand at each measurement position. For an instrument without compensation heaters said compensation voltage is superimposed on the voltage of either the first or the second heater.

In order to avoid artifacts said switching between the heaters or the compensation heaters should also be smooth and seamless.

Preferably, these restriction means comprise for each heater or for each compensation heater a voltage follower and a diode, wherein the diodes are oppositely orientated to the respective voltage followers. In an exemplary embodiment an operational amplifier can be used as voltage follower. Preferably the stabilization time of the operational amplifier is always small compared to the sampling frequency.

Another challenge when providing a thermoanalytical instrument comprising a first and a second compensation heater is to prevent the sensitivity of the second control loop from dropping to zero close to zero-crossings.

The second control loop can be controlled by the differential temperature between the first and the second measurement position, more precisely by a voltage proportional to said differential temperature. The required amount of compensation heating power is substantially proportional to this differential temperature, but the output of the second control loop is a voltage rather than a power.

The gain or sensitivity of the second control loop can be expressed as $$\frac{dP}{d(\Delta T)} = \frac{dP}{dU_C} \cdot \frac{dU_C}{d(\Delta U_{tp})} \cdot \frac{d(\Delta U_{tp})}{d(\Delta T)}$$
$$= \frac{2U_C}{R_C} \cdot C_{PID} \cdot \alpha_s$$

where $\Delta T$ is the differential temperature between the first and second measurement positions, $U_c$ the compensation voltage, $\Delta U_{tp}$ the differential thermopile voltage between the first and second measurement positions, $R_c$ the electrical resistance value of the active first or second compensation heater, $C_{PID}$ the gain factor of the second control loop comprising a PID controller and $\alpha_S$ is the Seebeck coefficient of the thermopile arrangement comprised in the sensor, which measures the temperature of the measurement position associated with the active compensation heater. This equation implies, that the overall gain of the second loop is proportional to the compensation voltage $U_C$ and can even drop to zero when said compensation voltage $U_C$ is zero. This situation—excluding headroom problems—cannot occur with power compensation as the second compensation heater is set to a fixed offset. On the other hand with dynamic compensation this situation can coincide with moments of switching between the compensation heaters and can manifest itself by a flattening of the compensation signal around zero-crossings.

According to a third aspect, the invention relates to a thermoanalytical instrument, in particular a DSC, wherein an input fed to the second control loop is substantially proportional to a voltage required by the active heater or active compensation heater in order to prevent a sensitivity drop of the second control loop to zero. The active heater or active compensation heater being the one which is supplied with said additional or compensation power.

The second control loop can further comprise a square root circuit, which takes the square root of the differential thermopile arrangement voltage prior to the PID controller. With this circuit the overall compensation gain of the second control loop would no longer be dependent on $U_C$ and can be expressed as $$\frac{dP}{d(\Delta T)} = \frac{dP}{dU_C} \cdot \frac{dU_C}{d(\sqrt{\Delta U_{tp}})} \cdot \frac{d(\sqrt{\Delta U_{tp}})}{d(\Delta T)}$$
$$= \frac{2U_C}{R_C} \cdot C_{PID} \cdot \frac{\alpha_S}{2 \cdot \sqrt{\Delta U_{tp}}}$$
$$\approx \frac{\alpha_S}{R_C} \cdot C_{PID}^2$$

An implementation of a square root circuit is especially suitable for use with a digital control loop. A square root circuit can also be realized for an analog control loop by adding a square root amplifier for each compensation heater to the second control loop. The addition of the square root circuit to an analog control loop is a less preferred solution, as it can constitute a possible source of added noise and instability.

Another approach to prevent the described sensitivity drop can be realized by providing a DSC with dynamic compensation, further comprising restriction means as well as means to supply an individual offset power in form of an offset voltage to each compensation heater.

Preferably, each compensation heater is fed an equal offset voltage value. For unequal values the offset temperature depends on the higher offset voltage, while the zero-crossing problem depends on the lower offset voltage. Both effects will decrease the accuracy of the measuring results.

The offset voltage value should be high enough to eliminate artifacts near zero-crossings and at the same time small enough to avoid the occurrence of any substantial offset temperature, which might limit the operational temperature range of the instrument. The offset voltage giving rise to the offset power should be chosen with regard to the actual instrument setup, the sample material and the properties of the parts constituting the instrument. In terms of the acceptable offset temperature $\Delta T_{off}$, the offset voltage $U_{off}$ can be expressed as $$U_{off} < \sqrt{\frac{R_c}{R_{th}} \cdot \Delta T_{off}}$$

where $R_c$ represents the value of the compensation heater resistance and $R_{th}$ represents the thermal resistance between the measurement positions and the environment.

A further challenge when implementing the dynamic compensation principle can be the occurrence of asymmetries, especially in a generally symmetrically operated thermoanalytical instrument comprising a first and a second compensation heater. The first as well as the second compensation heater can supply a compensation power to the respective first or second measurement position. Unfortunately, the compensation power of the second compensation heater has a direct influence on the temperature of the second measurement position, also referred to as reference position, especially when said second measurement position also receives the compensation power. This influences the first control loop, which is responsible for imposing the temperature program on the first and second measurement position, and can give rise to interference induced oscillation problems.

According to a fourth aspect the invention relates to a thermoanalytical instrument operated with the dynamic compensation principle with a first and a second control loop, wherein the two control loops have individual time constants.

The detuning of the time constants of the two control loops has the advantage that interference-induced oscillation problems can be avoided as only one control loop acts on a specific measurement position at any time.

Besides detuning the time constants, switching means can be included into the first and second control loop, which cause the temperature inputted into the first control loop to switch from the first temperature to the second temperature, when the second control loop switches from activating the second compensation heater to activating the first compensation heater and vice versa. Activation is understood in this context as allowing a compensation current to flow to the activated compensation heater. The switching of the input temperature can be linked to the switching of the second control loop. Through this measure it can be prevented that the first and the second control loop are simultaneously active on the same measurement position, whereby the aforementioned possibility of interference between the first and second control loop can be avoided.

For this measure the switching of both control loops should occur at the same time. Under this condition the alternative inputs—the first or second temperature—to the first control loop will have substantially the same magnitude at the moment of switching. This can be provided by the measure described above, linking both switching mechanisms to zero-crossings of the differential temperature.

Preferably, the dynamic compensation is used to control a thermoanalytical instrument, such as a DSC. Especially advantageous is the use with a chip-type differential scanning calorimeter, as highly symmetrical measurement positions can be realized. Further the thermoanalytical instrument can be an instrument which combines DSC and TGA (TGA: thermogravimetric analysis). A method according to the invention can be used to control either of these thermoanalytical instruments.

Another aspect of the invention relates to a method for controlling a thermoanalytical instrument, in particular a differential scanning calorimeter, wherein the thermoanalytical instrument comprises a first measurement position, a second measurement position, means for setting a predetermined temperature program of temperature target values versus time, a first heater associated with the first measurement position, a second heater associated with the second measurement position, a first sensor, which measures a temperature of the first measurement position, a second sensor, which measures a temperature of the second measurement position, and a controller. Said controller controls a heating power of said first heater so as to cause said measured first temperature to essentially follow said temperature program and additionally said controller controls said first and second heaters so as to essentially cause any difference between the first and second temperatures to become zero. Further the controller determines which of said first and second measured temperatures is lower and applies an additional power to the heater which is associated with the measurement position having said lower measured temperature.

In another exemplary embodiment the thermoanalytical instrument further comprises a first compensation heater associated with the first measurement position and a second compensation heater associated with the second measurement position. In this embodiment the temperature program can be applied to each measurement position by the respective heater, and the controller applies the additional power to the compensation heater associated with the cooler measurement position, i.e. the measurement position having the lower measured temperature.

Preferably, the application of the temperature program can be controlled by a first control loop and the compensation of the differential temperature can be controlled by a second control loop.

In another exemplary embodiment the compensation of the differential temperature is further controlled by restriction means comprised in the second control loop.

In another exemplary embodiment said dynamic compensation principle further comprises the step of applying an individual offset voltage to each compensation heater. Preferably, the same offset voltage is applied to each compensation heater.

Advantageously, a computer program for controlling a thermoanalytical instrument according to the invention with a method as described above is provided, wherein the computer program is stored in a memory device of the controller of the thermoanalytical instrument.

BRIEF DESCRIPTION OF THE DRAWINGS

The different embodiments of the invention are discussed in relation to the following figures, wherein similar elements in the figures are referred to with the same reference symbol and wherein.

DETAILED DESCRIPTION

Figure 1:
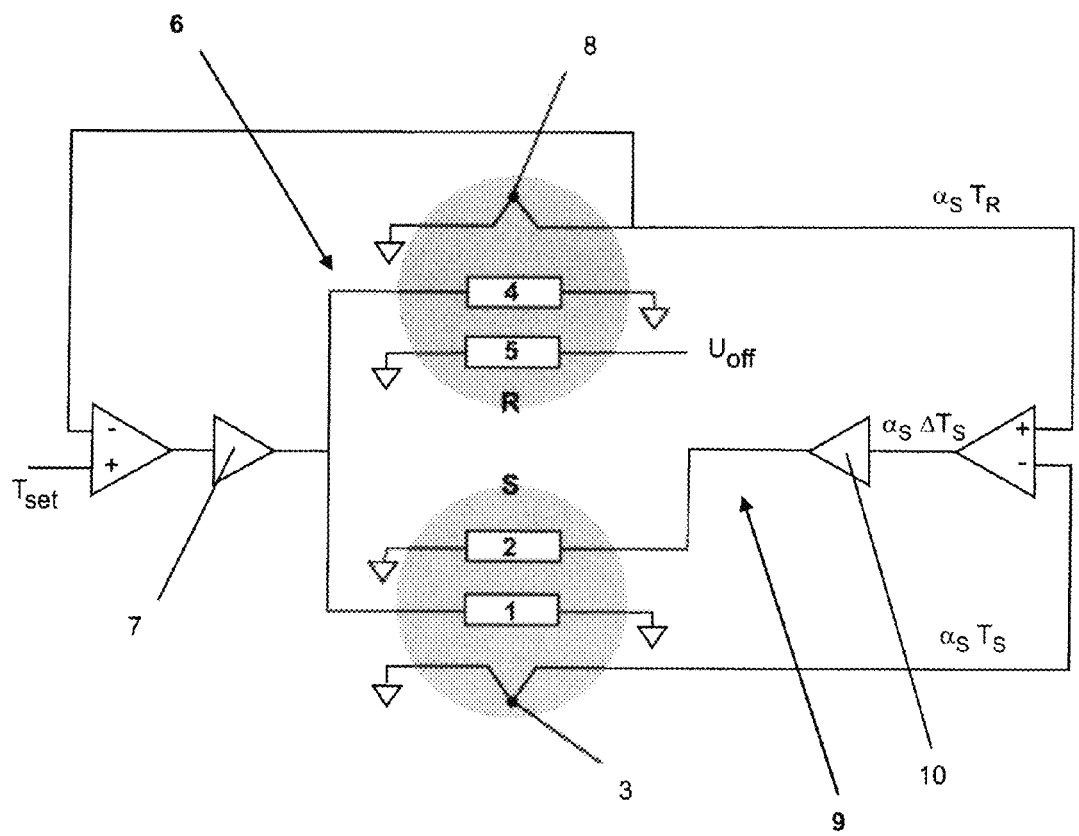
FIG. 1 is a schematic electronic circuit for a DSC with power compensation, as known in the prior art.

FIG. 1 shows an electronic setup for a DSC with power compensation, as known in the prior art. The DSC comprises at least two measurement positions, a first measurement or sample position S and a second measurement or reference position R. A sample or sample material can be placed on the sample position S and a reference material can be placed on the reference position R. Experiments on a sample can be performed with and without a reference material.

The sample position S is in thermal contact with a sample heater 1 and a first compensation heater 2. The temperature at the sample position S is determined by a sensor comprising at least one thermocouple 3. Likewise the reference position R is in thermal contact with a reference heater 4 and a second compensation heater 5, which supplies an offset power arising from a constant offset voltage $U_{off}$. The temperature at the reference position R is determined with a sensor comprising at least one thermocouple 8. The heaters 1, 2, 4, 5 are preferably designed as individual resistance heaters.

The sample heater 1 and the reference heater 4 apply a temperature program to the respective measurement positions S, R and are part of a first control loop 6. This control loop 6 also comprises a PID controller 7. The temperature program is fed to the first control loop 6 as indicated by the temperature set points $T_{set}$.

The first compensation heater 2 is integrated in a second control loop 9, which also comprises a PID controller 10. The compensation voltage supplied to the sample position S gives rise to a compensation power and its magnitude is chosen in order to control any temperature difference ΔT between the sample position S and the reference position R to remain substantially zero. Therefore, the input to the second control loop 9 is the product of said temperature difference ΔT and the Seebeck constant of the thermopile $α_S$. The control loops 6, 9 are connected with a main controller for controlling the DSC, which is not shown here.

Figure 2:
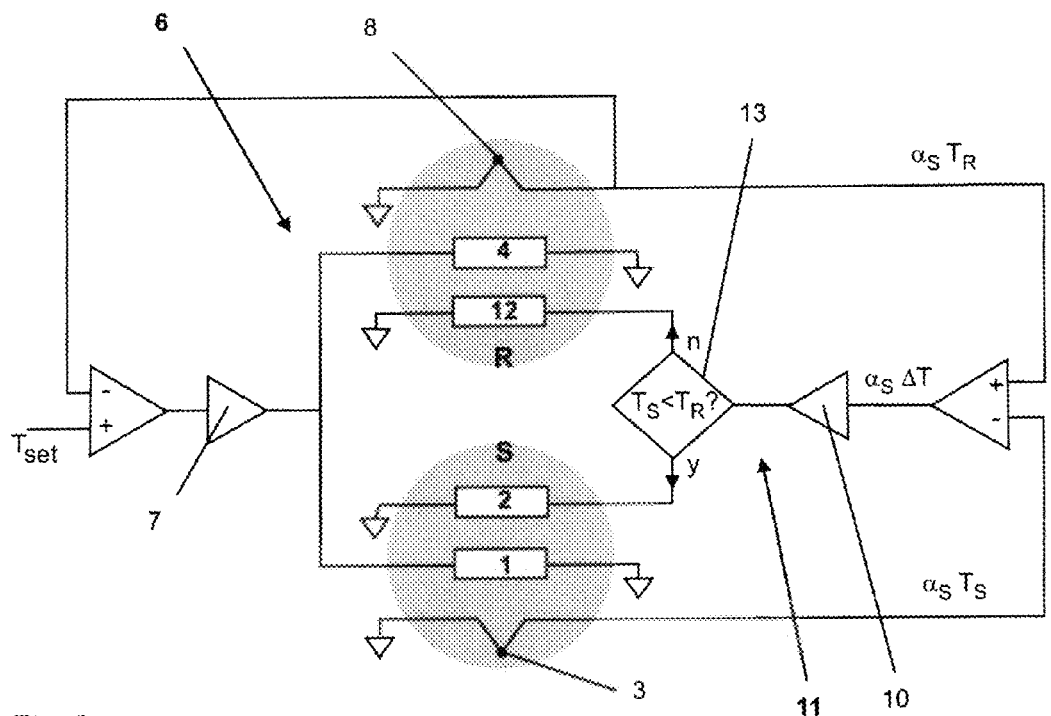
FIG. 2 is a schematic electronic circuit for a DSC with dynamic compensation, wherein the DSC comprises a heater and a compensation heater for each measurement position.

FIG. 2 shows an electronic setup for a DSC with a compensation according to the invention, which will be referred to as dynamic compensation and shares some features with the power compensated DSC of FIG. 1. For the dynamic compensation as shown in FIG. 2 a second control loop 11 comprises besides a first compensation heater 2 and a PID controller 10 also a second compensation heater 12, which is in thermal contact with the reference position R. The second control loop 11 further comprises determination means 13, which allow selecting the first compensation heater 2 or the second compensation heater 12 to receive a compensation voltage, which is applied to the respective measurement position and gives rise to a compensation power. Which of the two compensation heaters 2, 12 receives the compensation voltage depends on the sign of the differential temperature ΔT between the sample position S and the reference position R. If the temperature difference $ΔT=T_S-T_R$ is negative, because the temperature $T_R$ at the reference position is higher than the temperature $T_S$ at the sample position, the compensation voltage applied to the first compensation heater 2 is raised and thus compensation power is applied to said first compensation heater 2, which leads to an increase of the sample temperature $T_S$ in order to reduce the differential temperature ΔT to substantially zero again. If the sign of the differential temperature ΔT is positive, the compensation voltage applied to the second compensation heater 12 is raised in order to reduce the differential temperature ΔT to substantially zero.

Figure 3:
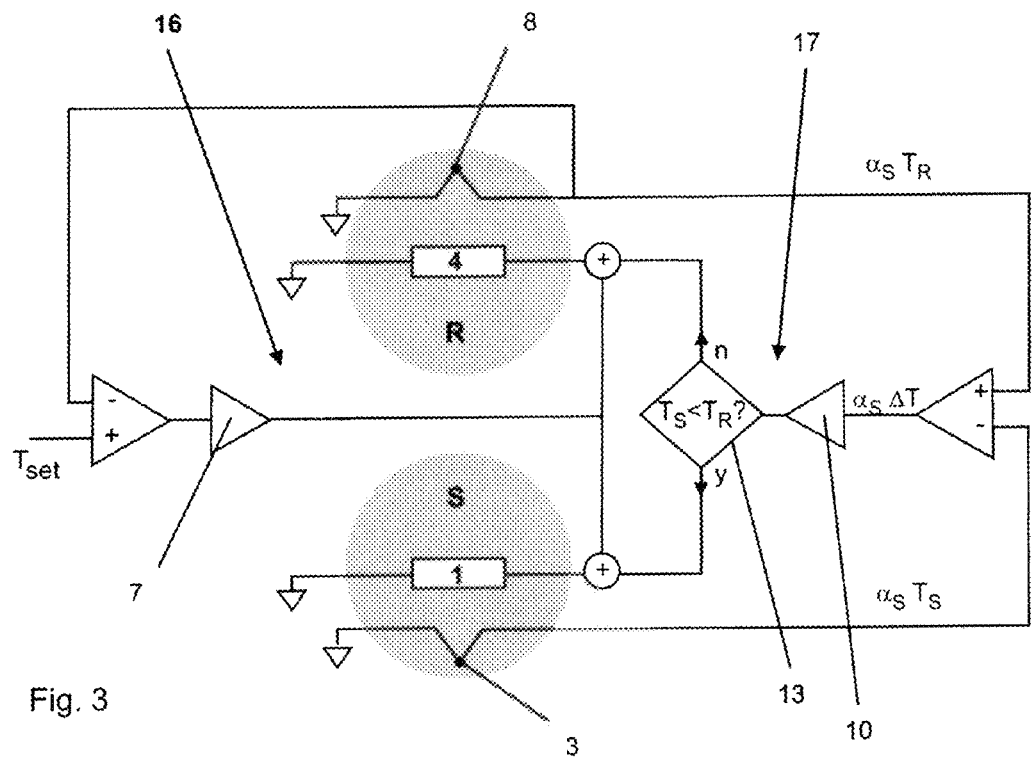
FIG. 3 is schematic electronic circuit for a DSC with dynamic compensation, wherein the DSC comprises a heater for each measurement position.

FIG. 3 shows another electronic setup for a DSC with dynamic compensation without compensation heaters. Each measurement position S, R is equipped with a main heater 1, 4 and at least one thermocouple 3, 8 as already described in FIG. 2. The main heaters 1, 4 are on one hand controlled by a first control loop 16, which supplies a temperature program $T_{set}$ to the measurement position S, R, and on the other hand by a second control loop 17, which comprises similar parts as the one described in FIG. 2. Due to a differential temperature ΔT determined from the thermocouples 3, 8 an extra heating power is supplied to either the sample position S or the reference position R through the second control loop 17. This extra heating power is electronically added to the main heating power delivered by the first control loop 16 to the respective main heater 1, 4.

Figures 4A, 4B:
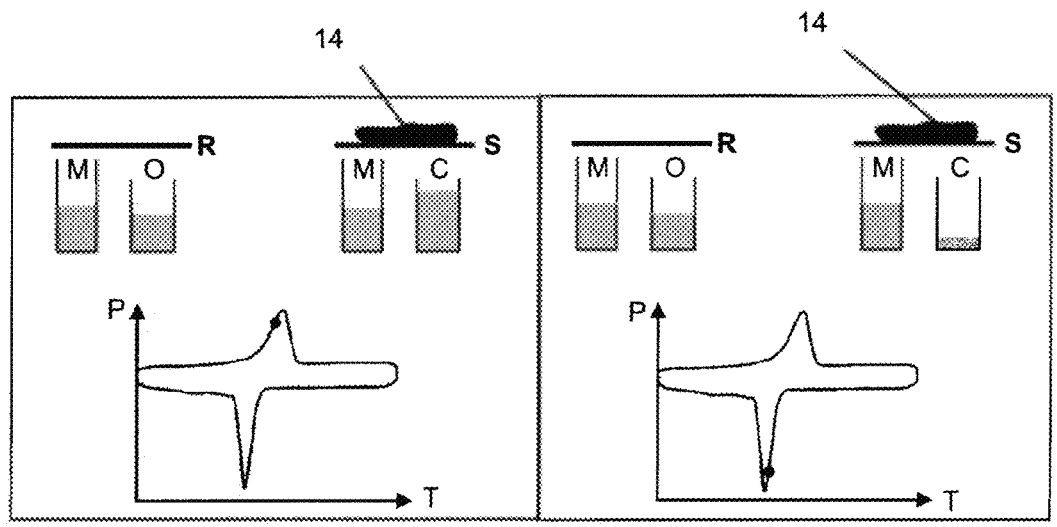
FIGS. 4a and 4b are representations of the sample and reference heater power, the reference offset power demand and the compensation power demand of a DSC with power compensation, with FIG. 4a showing melting of polypropylene and FIG. 4b showing crystallization of polypropylene.
Figures 5A, 5B:
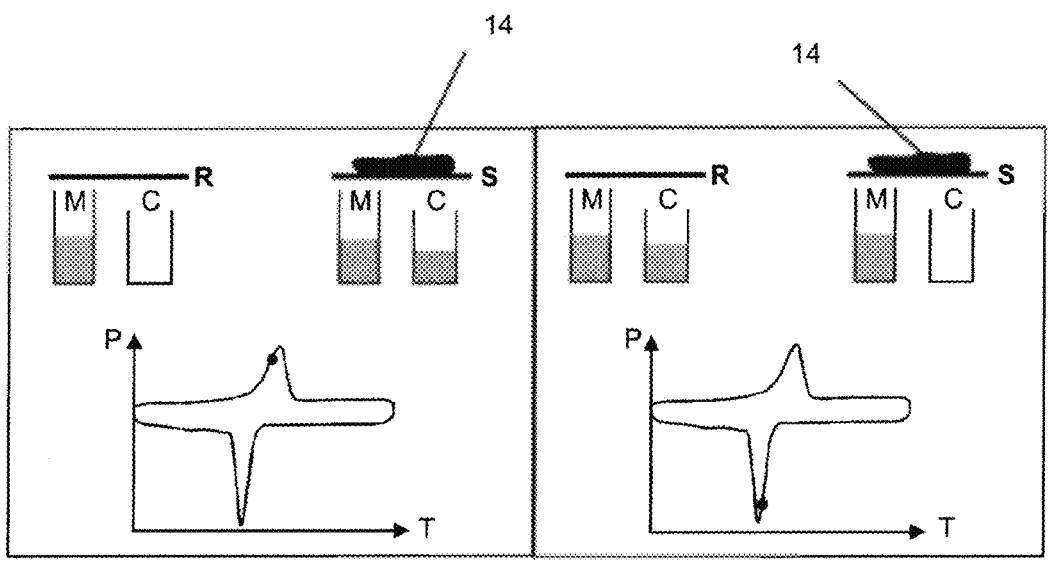
FIGS. 5a and 5b representations of the sample and reference heater power, the reference compensation power demand and the sample compensation power demand of a DSC with dynamic compensation, with FIG. 5a showing melting of polypropylene and FIG. 5b showing crystallization of polypropylene.

In FIGS. 4 and 5, the known power compensation principle is compared on a highly abstract level with the dynamic compensation according to the invention. FIG. 4a shows the heating power distribution at the marked point of a melting curve of a polypropylene sample 14 subjected to a power compensated DSC experiment. FIG. 4b shows the heating power distribution at the marked point of a crystallization curve of a polypropylene sample 14 subjected to a power compensated DSC. FIGS. 5a and 5b show the heating power distribution at the same point of a melting or respectively a crystallization curve of a polypropylene sample 14 subjected to a dynamic compensated DSC experiment.

During the experiments shown in FIGS. 4a and 4b the sample position S as well as the reference position R are subjected to a temperature program through the sample and reference heater. The voltage supplied by the sample heater and the reference heater at the marked point of the curve is indicated with the reference symbol M. Additionally, the second compensation heater supplies a constant offset voltage O to the reference position R throughout the experiment. To compensate any temperature changes of the sample due to a phase transition a compensation voltage C is also supplied to the sample position S, which is controlled in order to keep the differential temperature between the sample position S and the reference position R substantially zero. At the marked point on the melting curve the first compensation heater is supplied with a compensation voltage C being higher than the offset voltage O, while at the marked point of the crystallization curve the compensation voltage C is lower than the offset voltage O. Because both points mark roughly the same temperature, the main heater voltage M is approximately equal in both situations.

When comparing the situation shown in FIGS. 4a and 4b for power compensation with the situation shown in FIGS. 5a and 5b for dynamic compensation it is evident, that the overall compensation power is strongly reduced, leading to an improved signal-to-noise-ratio. At the point on the melting curve in FIG. 5a only the first compensation heater applies any compensation power, while the second compensation heater is inactive. The situation at the marked point of the crystallization curve in FIG. 5b is reversed.

The dynamic compensation has the advantage that the compensation power as compensation voltage is only applied where and when it is needed, leading to the already mentioned advantages of increased headroom and an absence of an offset temperature.

Figure 6:
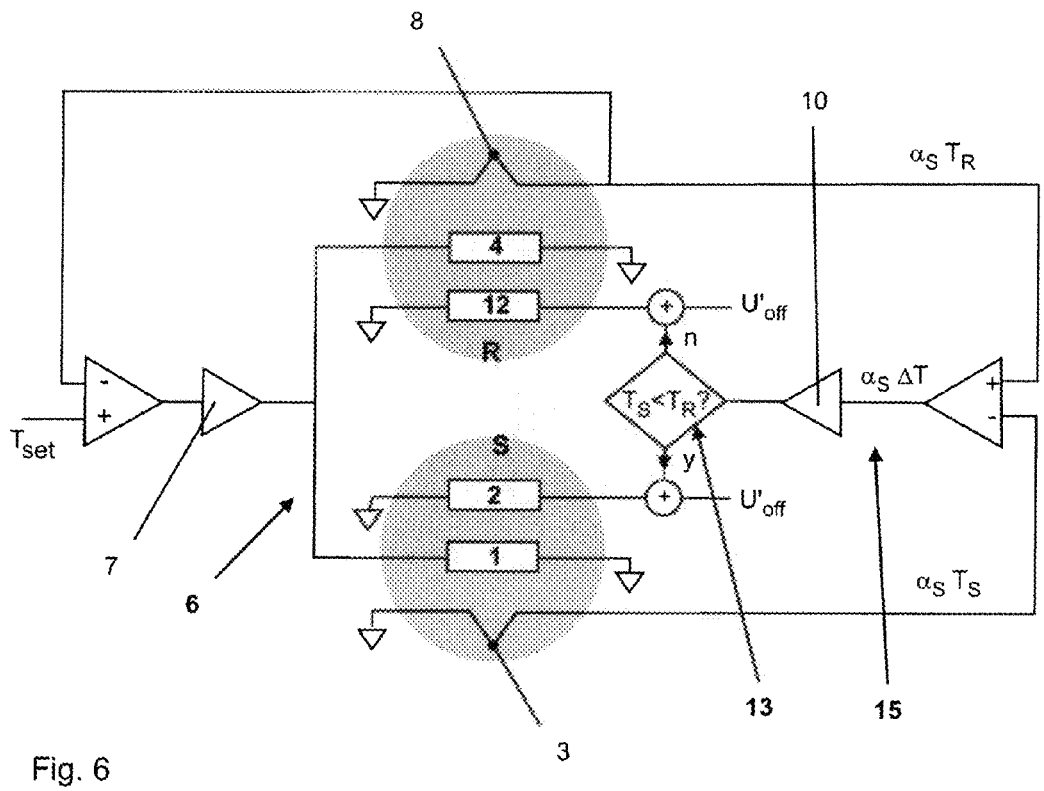
FIG. 6 is a schematic electronic circuit for a DSC with dynamic compensation comprising means for controlling a switching of the compensation heaters and an offset voltage applied to each compensation heater.

FIG. 6 shows a further electronic setup for a DSC with dynamic compensation, which is similar to the setup of FIG. 2, but where a constant offset voltage U'$_{off}$ is supplied to the first compensation heater 2 as well as to the second compensation heater 12. The offset voltage U'$_{off}$ in a chip-calorimeter setup according to the invention can for example be about 0.5 V, which corresponds to about 50 μW of heating power based on a compensation heater with a resistance of about 5 kΩ. A thermal resistance of the order of 0.01 K/μW, a typical magnitude in such a chip-calorimeter setup, will result in a very small offset temperature of only about 0.5° C. The exact amount for the offset voltage U'$_{off}$ depends e.g. on the quality of the PID controller, the setup, etc. The offset voltage U'$_{off}$ should be chosen in such a way that it is high enough to prevent artifacts without adding a significant temperature offset to the baseline.

Figure 7:
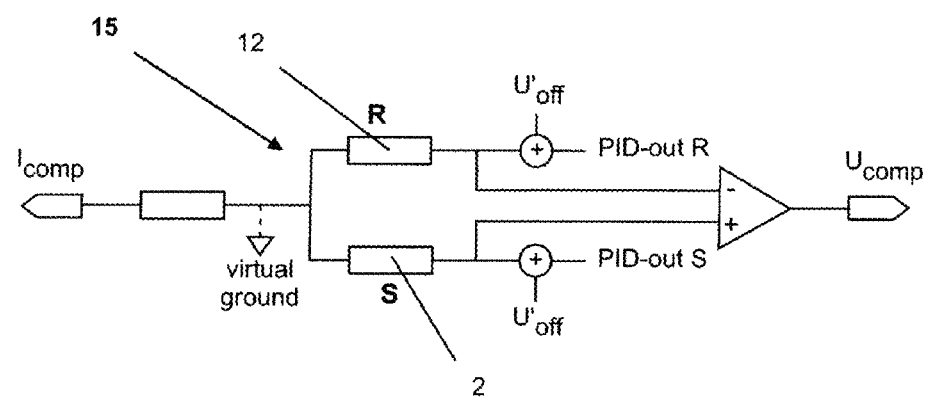
FIG. 7 is a schematic electronic circuit for the data acquisition of a DSC with dynamic compensation comprising means for controlling a switching of the compensation heaters and an offset voltage applied to each compensation heater.

Because of the dynamic compensation according to the invention the data acquisition has to be adapted. For power compensation the compensation power is acquired by measuring the voltage across and the current through the compensation heater. As for the dynamic compensation, where the heating power is alternatively delivered to one or the other of the two measurement positions, an extraction of individual signals, such as compensation voltage and compensation current, at one fixed point in the circuit is no longer possible. To overcome this problem the data acquisition for a thermoanalytical instrument with a first and a second compensation heater comprises: Measuring the voltage U$_{comp}$ differentially across both compensation heaters and measuring the current I$_{comp}$ additively as the sum of the compensation heaters currents. For dynamic compensation with additional compensation offset power this is schematically shown in the circuit diagram of FIG. 7 showing the second control loop 15 of FIG. 6 in more detail. For this setup the net compensation power is given by the difference of the power P$_S$ of the first compensation heater 2 and the power P$_R$ of the second compensation heater 12 as $$P_{comp} = P_S - P_R = U_S I_S - U_R I_R,$$

with the offset contribution of the inactive compensation heater being always small in comparison to the active one, but due to the applied compensation offset voltage not negligible. The net compensation power P$_{comp}$ is the signal of interest. What is actually measured, however, can be expressed as:

$$P_{meas} = (U_S - U_R) \cdot (I_S + I_R) = (U_S I_S - U_R I_R) + (U_S I_R - U_R I_S)$$

$$= P_{comp} + U_S U_R \left( \frac{1}{R_R} - \frac{1}{R_S} \right)$$

with R$_S$ being the heater resistance of the first compensation heater 2 and R$_R$ that of the second compensation heater 12.

Because the sample position S and the reference position R remain at approximately equal temperatures during a dynamic compensation experiment and should possess an intrinsic symmetry, it can be assumed that the resistance values are well matched. Therefore the error term $(U_S U_R (R_R^{-1} - R_S^{-1}))$ of the actual net compensation power will be quite small compared to the net compensation power signal and can be neglected.

Figure 8:
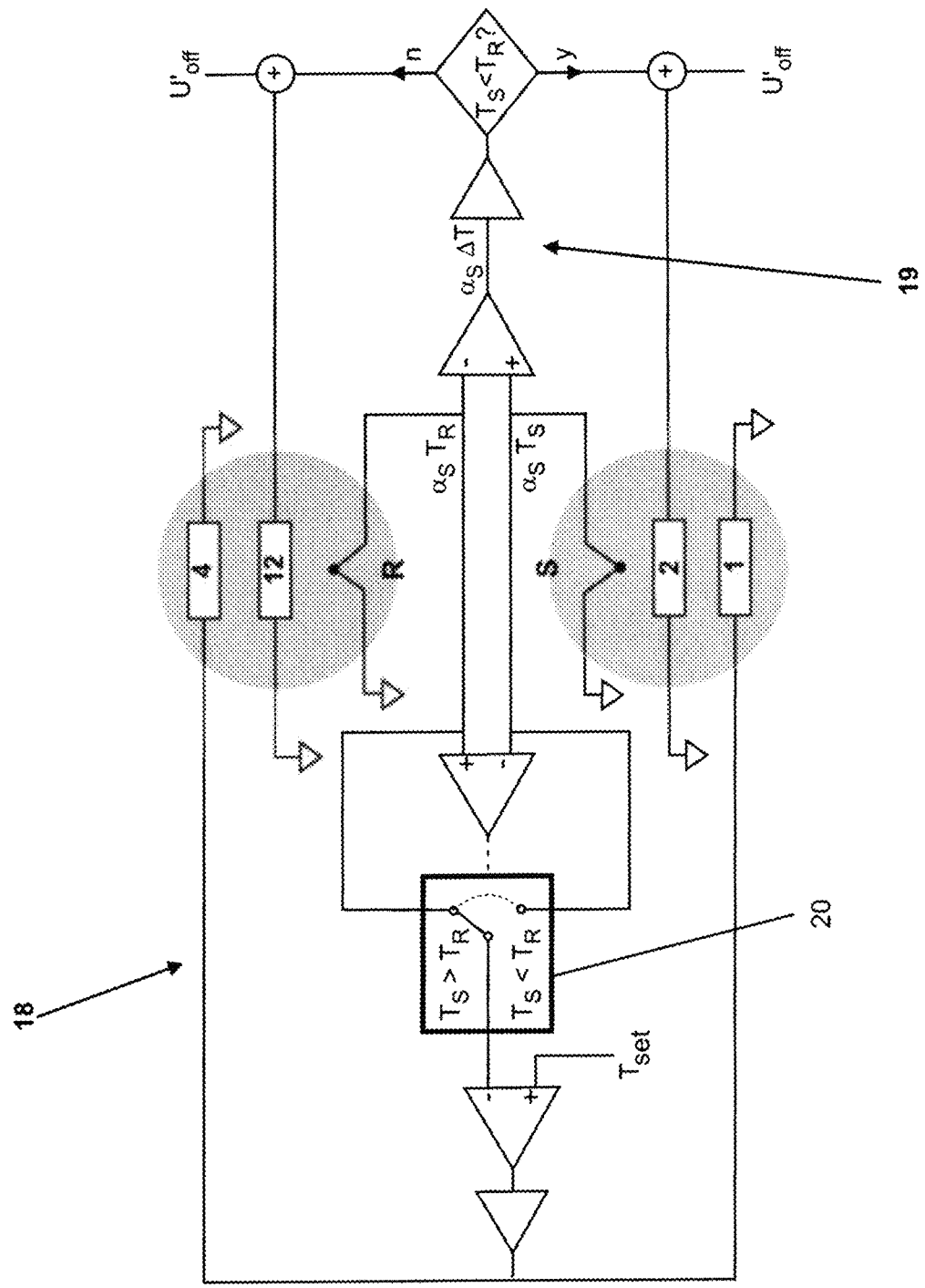
FIG. 8 an electronic setup for a DSC with dynamic compensation and induced switching of the temperature input into the first control loop in relation to the measurement position controlled by the second control loop.

FIG. 8 shows an electronic setup of a further DSC with dynamic compensation, wherein interference between a first control loop 18 and a second control loop 19 is prevented by introducing switching means 20. The same decision criterion being used to activate the appropriate compensation heater 2, 12 on measurement positions R or S is also fed into the first control loop 18 via the switching means 20, which controls the temperature T$_S$, T$_R$ to be used for controlling said first loop 18. Through this measure only one control loop 18, 19 is active at one of the measurement positions S, R. When the control of the second control loop 19 switches to the other measurement position S, R, the control of the first control loop 18 is simultaneously switched to the opposite measurement position.

Figure 9:
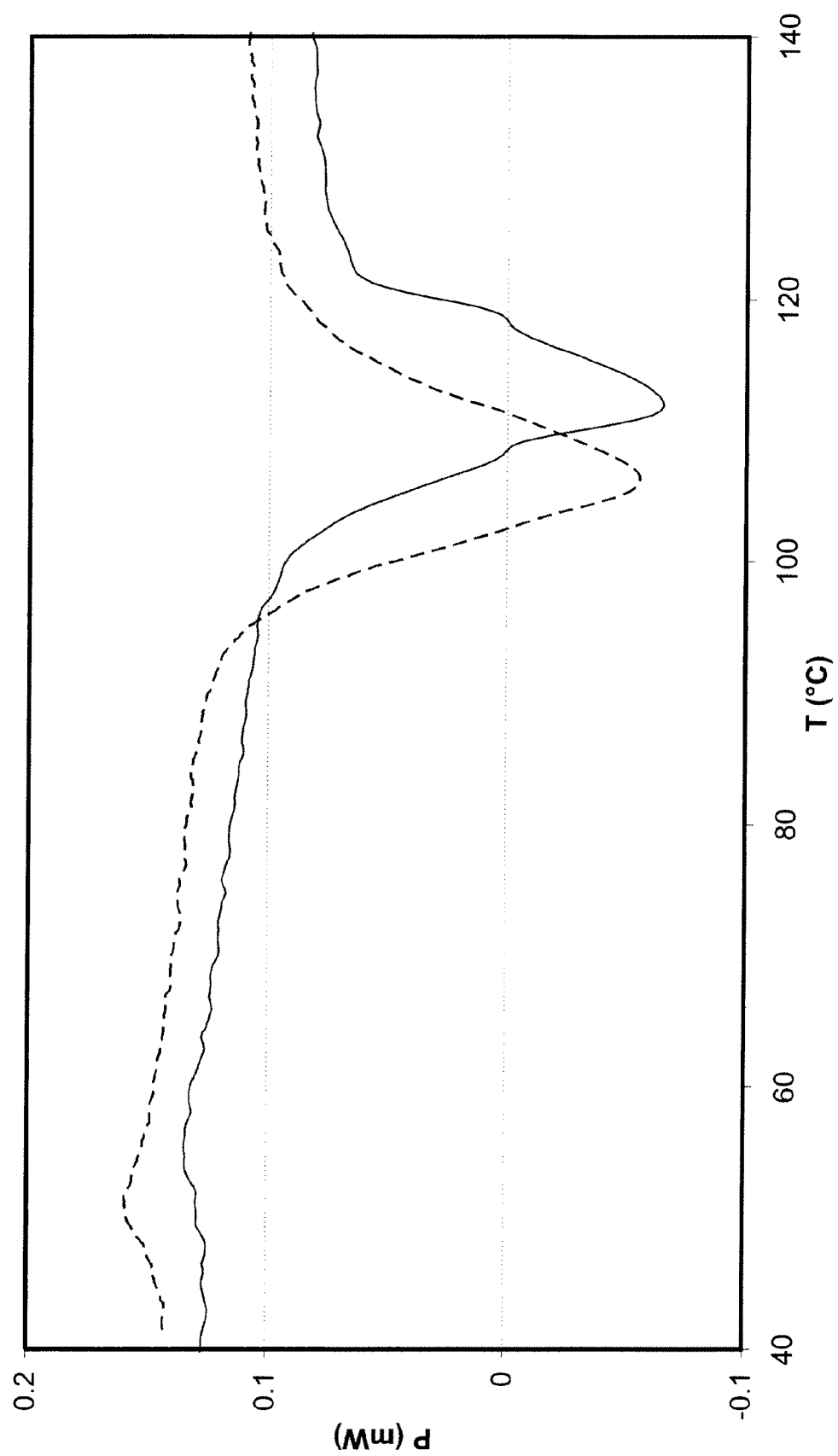
FIG. 9 presents comparative measurements of the cold crystallization of polyamide 6 showing the advantage of means for preventing a sensitivity drop of the second control loop.

FIG. 9 shows comparative experiments on the cold crystallization of polyamide 6 subjected to DSC with dynamic compensation and a heating rate of 50° C./s. The solid line graph represents a measurement without an additional compensation voltage offset U'$_{off}$ and the dotted line graph a measurement with an additional compensation voltage U'$_{off}$ applied to both compensation heaters 2, 12. It is evident from FIG. 9 that the artifacts present around a power of 0 mW in the solid line graph do not appear in the dotted line graph, thereby showing the advantages of applying said additional compensation voltage offset U'$_{off}$.

Figure 10:
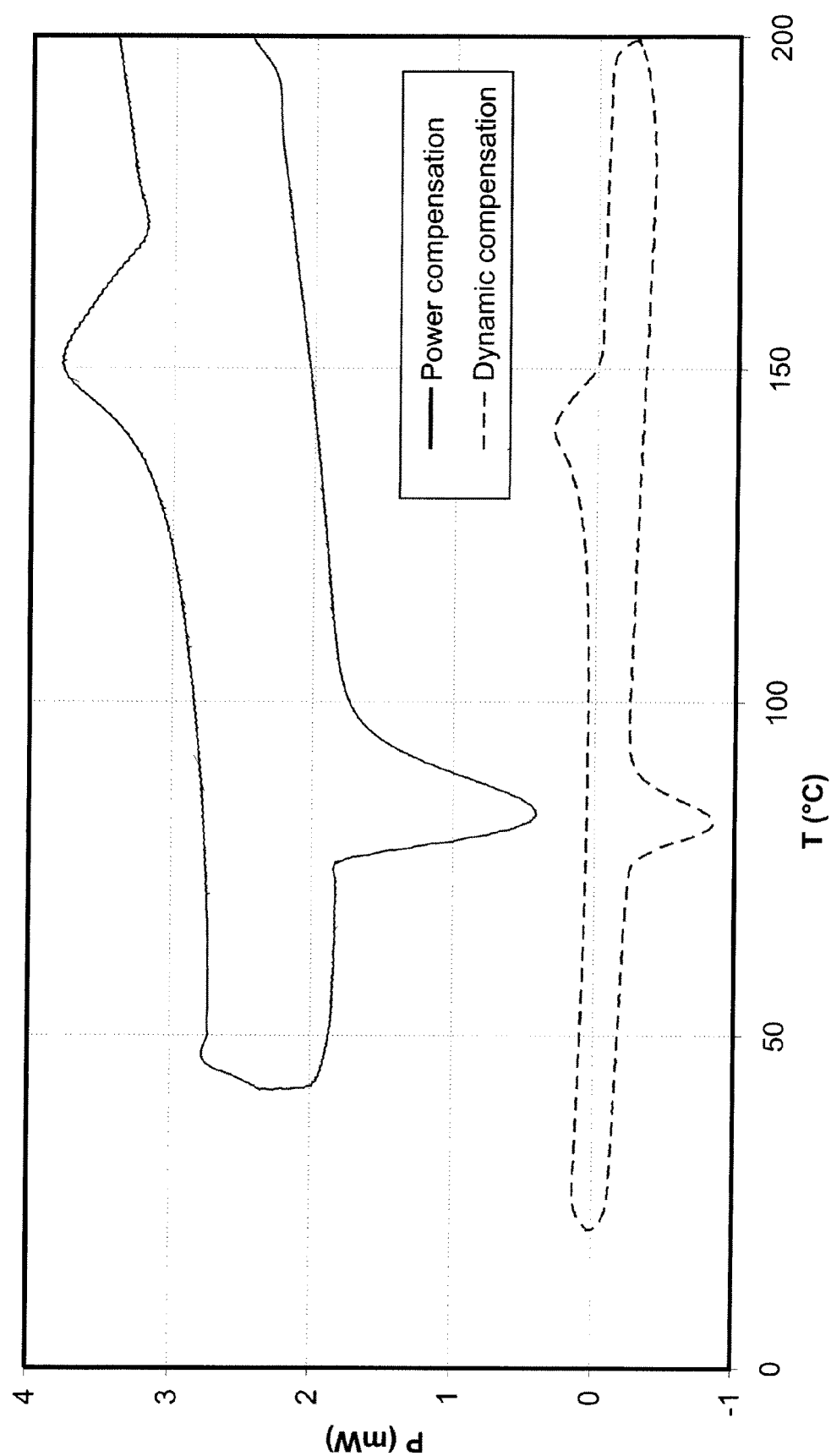
FIG. 10 presents DSC measurements on polypropylene showing the advantage in offset temperature, baseline offset, drift and curvature of dynamic compensation in comparison to power compensation.
Figure 11:
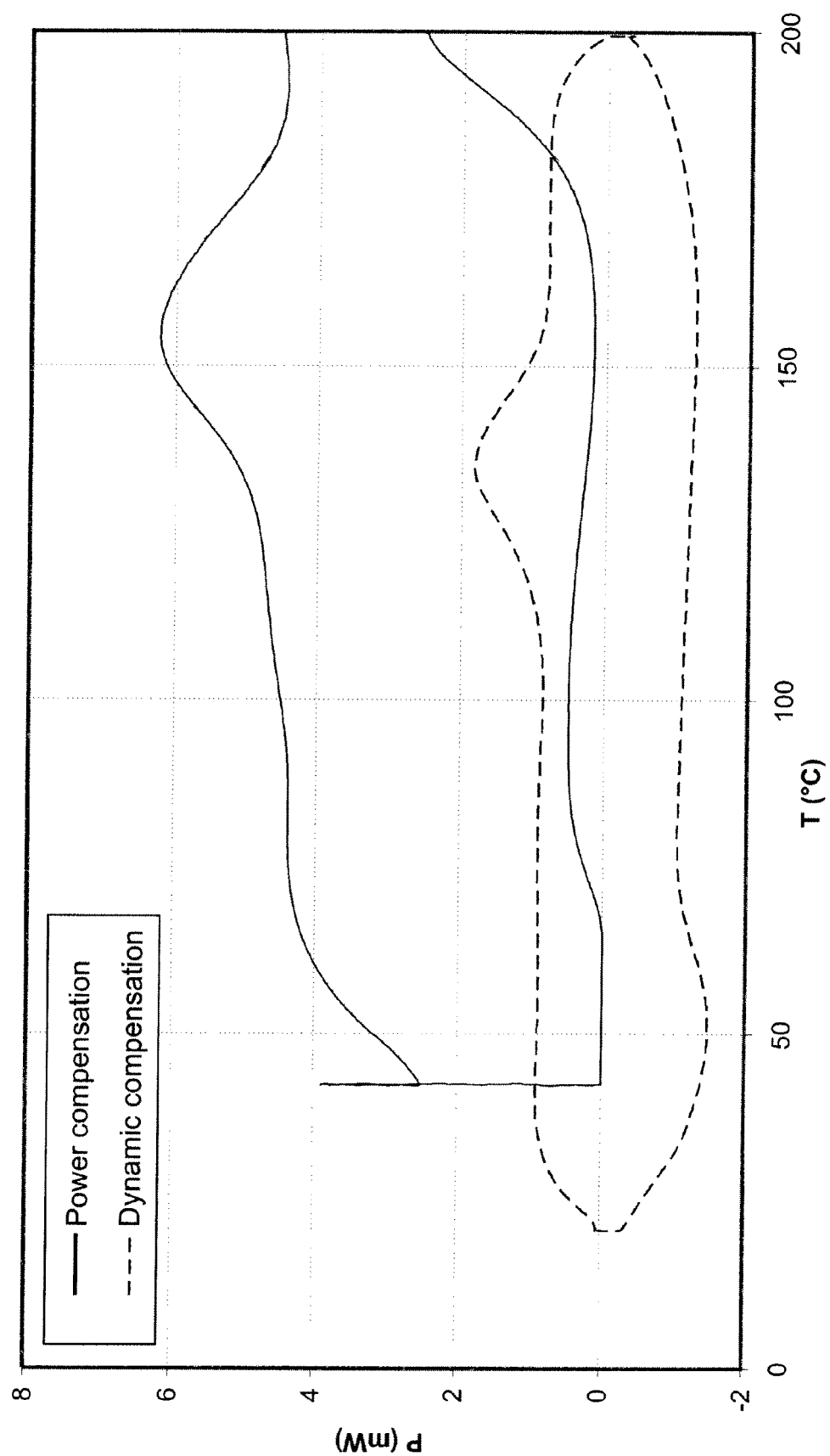
FIG. 11 presents DSC measurements on polypropylene showing the headroom advantage of the dynamic compensation in comparison to power compensation.

In order to prove the advantages of dynamic compensation over power compensation the results of comparative heating/cooling experiments on polypropylene are presented in FIGS. 10 and 11. The solid line graph was measured with power compensation and the dotted line graph with dynamic compensation comprising means to control the switching between the compensation heaters and an additional compensation offset voltage.

The graphs presented in FIGS. 10 and 11 show that with dynamic compensation there is less to no offset from room temperature, less to no offset and slope in the baseline and the headroom trouble was also eliminated.

The principle of dynamic compensation is especially useful for chip-type differential scanning instruments but could also be adapted to other thermoanalytical instruments which so far utilize the power compensation principle.

What is claimed is:

1. A thermoanalytical instrument, in particular a differential scanning calorimeter, comprising:
   a first and a second measurement position;
   a first and a second heater, each heater associated with the corresponding measurement position;
   a first and a second compensation heater, each compensation heater associated with directly heating the corresponding measurement position;
   a first and a second sensor, for measuring a temperature at the corresponding measurement position; and
   a controller, comprising:
      means for setting a predetermined temperature program of temperature target values versus time;
      a first control loop for controlling the application of the temperature program to the first and second heaters;
      means for determining the lower of the temperatures measured at the first and second measurement positions; and
      a second control loop for controlling the compensation of the differential temperature between the first and the second measurement position by applying an extra heating power to the measurement position having the lower measured temperature, by a means for restricting the extra heating power to only the corresponding compensation heater at any point in time, wherein the means for restricting comprises, for each heater and compensation heater:
a voltage follower; and
a diode, oppositely orientated to the voltage follower with which it is associated.

2. The thermoanalytical instrument of claim 1, wherein:
the controller comprises at least one PID controller.

3. The thermoanalytical instrument of claim 1, wherein:
the controller comprises a fuzzy control system.

4. The thermoanalytical instrument of claim 1, wherein:
each of the first and the second sensors comprises a thermopile arrangement with at least one thermocouple.

5. The thermoanalytical instrument of claim 1, wherein:
the second control loop is provided an input that is substantially proportional to a voltage required by the compensation heater that is to be supplied with additional power.

6. The thermoanalytical instrument of claim 5, wherein:
the second control loop comprises a square root circuit.

7. The thermoanalytical instrument of claim 1, wherein:
the means associated with the controller is arranged to supply each compensation heater with an individual offset voltage.

8. The thermoanalytical instrument of claim 1, wherein:
the first and second control loops have different time constants.

9. The thermoanalytical instrument of claim 1, further comprising:
a switch, in the controller, that controls the temperature input provided to the first control loop when the second control loop switches from activating the second compensation heater to activating the first compensation heater or vice versa.

* * * * *